United States Patent
Mohamed et al.

(10) Patent No.: US 8,152,820 B2
(45) Date of Patent: Apr. 10, 2012

(54) MEDICAL DEVICE AND METHOD FOR HUMAN TISSUE AND FOREIGN BODY EXTRACTION

(75) Inventors: Ziad Mohamed, Gainesville, GA (US); Timothy D. McDonald, Gainesville, GA (US)

(73) Assignee: Dai-Z, LLC, Gainesville, GA (US)

( * ) Notice: Subject to any disclaimer, the term of this patent is extended or adjusted under 35 U.S.C. 154(b) by 319 days.

(21) Appl. No.: 12/147,105

(22) Filed: Jun. 26, 2008

(65) Prior Publication Data
US 2009/0326546 A1 Dec. 31, 2009

(51) Int. Cl.
*A61B 17/24* (2006.01)
(52) U.S. Cl. ........................................................ 606/114
(58) Field of Classification Search .................. 606/113, 606/114, 127, 128, 110
See application file for complete search history.

(56) References Cited

U.S. PATENT DOCUMENTS

| | | | |
|---|---|---|---|
| 4,909,782 A | 3/1990 | Semm et al. | |
| 5,143,082 A | 9/1992 | Kindberg et al. | |
| 5,197,968 A * | 3/1993 | Clement | 606/115 |
| 5,224,930 A | 7/1993 | Spaeth et al. | |
| 5,279,539 A | 1/1994 | Bohan et al. | |
| 5,308,327 A | 5/1994 | Heaven et al. | |
| 5,312,416 A | 5/1994 | Spaeth et al. | |
| 5,320,627 A | 6/1994 | Sorensen et al. | |
| 5,330,483 A | 7/1994 | Heaven et al. | |
| 5,337,754 A | 8/1994 | Heaven et al. | |
| 5,403,276 A | 4/1995 | Schechter et al. | |
| 5,465,731 A | 11/1995 | Bell et al. | |
| RE35,164 E | 3/1996 | Kindberg et al. | |
| 5,514,150 A * | 5/1996 | Rostoker | 606/159 |
| 5,524,633 A | 6/1996 | Heaven et al. | |
| 5,554,151 A | 9/1996 | Hinchliffe | |
| 5,643,304 A | 7/1997 | Schechter et al. | |
| 5,647,372 A | 7/1997 | Tovey et al. | |
| 5,669,876 A | 9/1997 | Schechter et al. | |
| 5,669,937 A | 9/1997 | Boebel et al. | |
| 5,766,177 A | 6/1998 | Lucas-Dean et al. | |
| 5,830,231 A | 11/1998 | Geiges, Jr. | |
| 5,891,153 A * | 4/1999 | Peterson | 606/107 |
| 5,906,615 A | 5/1999 | Thompson | |

(Continued)

OTHER PUBLICATIONS

International Search Report for PCT application PCT/US2009/048098; 9 pages.

*Primary Examiner* — Ryan Severson
*Assistant Examiner* — Jonathan W Miles
(74) *Attorney, Agent, or Firm* — Gardner Groff Greenwald & Villanueva

(57) ABSTRACT

A coaxial tube assembly, a bag, a bag-translating assembly, a de-bulking tool, and a drive assembly. The bag is delivered into a cavity in a patient's body either manually for open surgery or through the coaxial tube assembly by operation of the drive assembly for minimally invasive surgery. After a mass of tissue is placed in the bag, which is now secured to the bag-translating assembly, the drive assembly is operated to activate the bag-translation assembly to retract the bag into the annular space of the coaxial tube assembly. As the bag is being retracted, the mass in the bag is pulled into engagement with the de-bulking tool, which extends through the lumen of the coaxial tube assembly. The drive assembly activates the de-bulking tool to morcellate the mass in the bag and convey the morcellated bits of the mass through the lumen of the coaxial tube assembly.

27 Claims, 15 Drawing Sheets

U.S. PATENT DOCUMENTS

| | | | |
|---|---|---|---|
| 6,024,751 A | 2/2000 | Lovato et al. | |
| 6,036,681 A | 3/2000 | Hooven | |
| 6,080,175 A | 6/2000 | Hogendijk | |
| 6,123,665 A * | 9/2000 | Kawano | 600/104 |
| 6,156,049 A | 12/2000 | Lovato et al. | |
| 6,159,160 A | 12/2000 | Hsei et al. | |
| 6,174,317 B1 | 1/2001 | Engman | |
| 6,193,715 B1 | 2/2001 | Wrublewski et al. | |
| 6,221,006 B1 | 4/2001 | Dubrul et al. | |
| 6,344,026 B1 | 2/2002 | Burbank et al. | |
| 6,350,267 B1 | 2/2002 | Stefanchik | |
| 6,406,440 B1 | 6/2002 | Stefanchik | |
| 6,506,166 B1 | 1/2003 | Hendler et al. | |
| 6,508,773 B2 | 1/2003 | Burbank et al. | |
| 6,537,273 B1 | 3/2003 | Sosiak et al. | |
| 6,602,265 B2 | 8/2003 | Dubrul et al. | |
| 6,659,105 B2 | 12/2003 | Burbank et al. | |
| 6,676,658 B2 | 1/2004 | Burbank et al. | |
| 6,695,858 B1 | 2/2004 | Dubrul et al. | |
| 6,971,988 B2 | 12/2005 | Orban, III | |
| 7,004,945 B2 | 2/2006 | Boyd et al. | |
| 7,135,018 B2 | 11/2006 | Ryan et al. | |
| 7,229,418 B2 | 6/2007 | Burbank et al. | |
| D547,798 S | 7/2007 | Dixon | |
| D548,783 S | 8/2007 | Dixon | |
| D548,784 S | 8/2007 | Dixon | |
| D549,281 S | 8/2007 | Dixon | |
| 2007/0021754 A1 * | 1/2007 | Chernenko et al. | 606/128 |

* cited by examiner

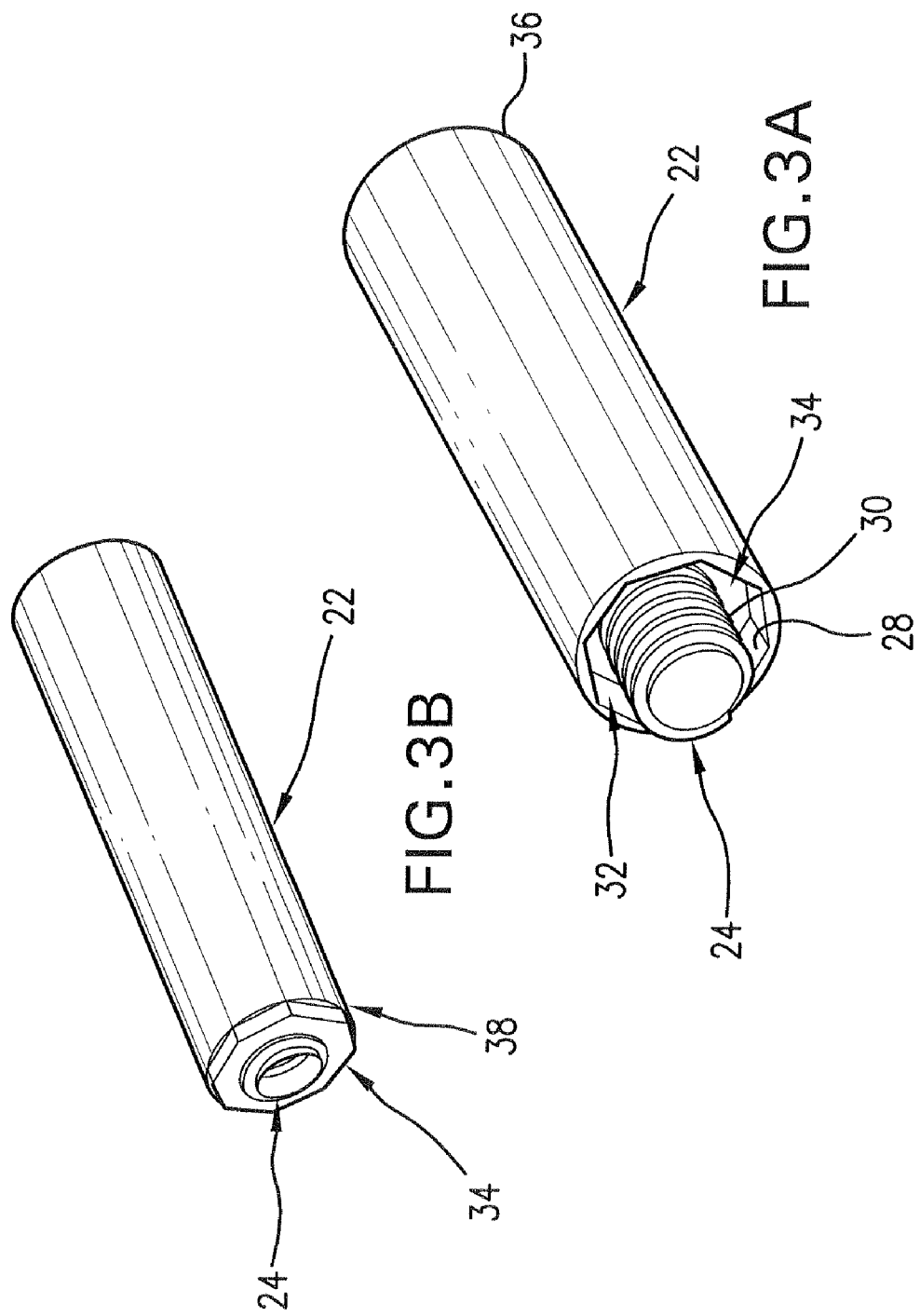

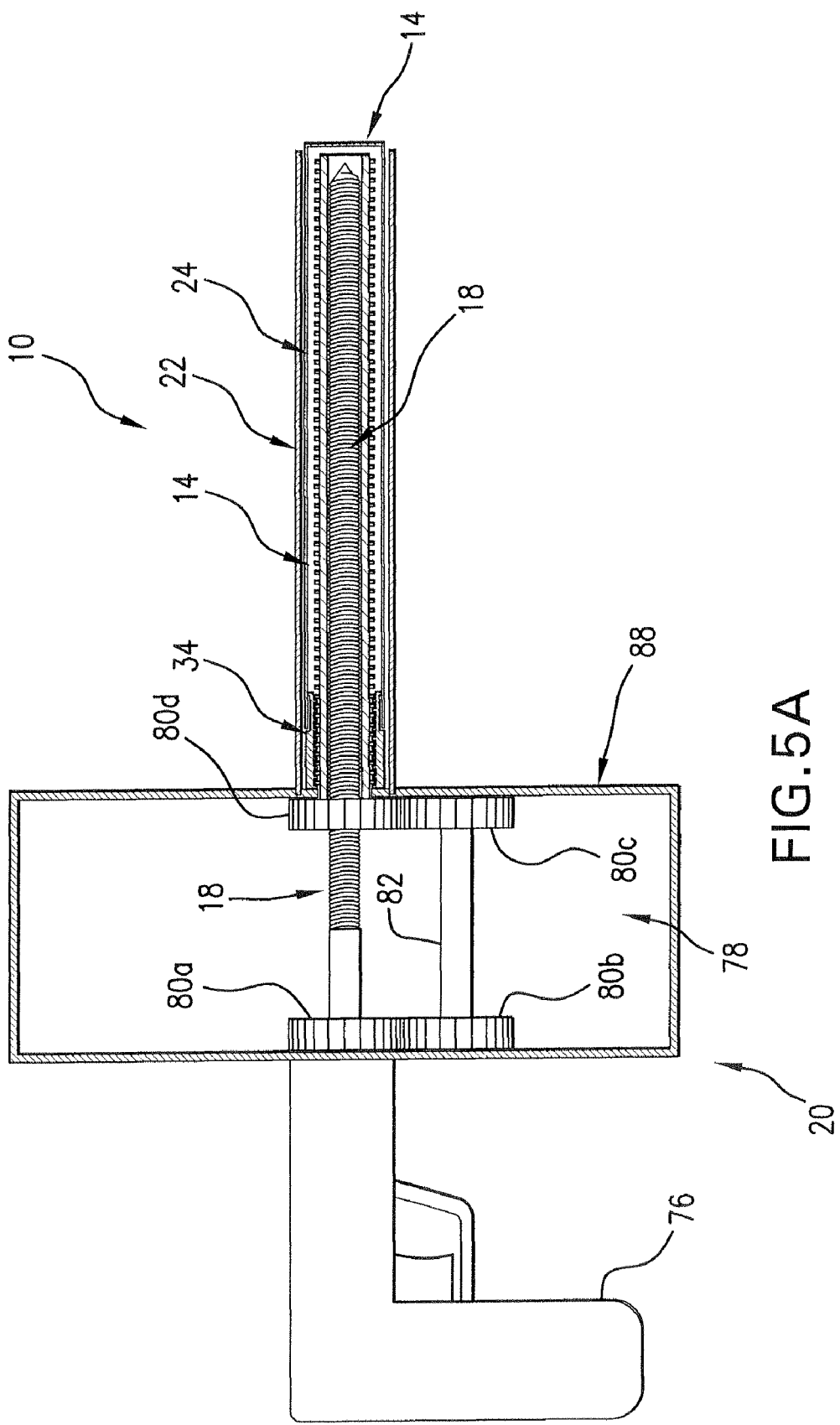

MEDICAL DEVICE AND METHOD FOR HUMAN TISSUE AND FOREIGN BODY EXTRACTION

TECHNICAL FIELD

The present invention relates generally to medical devices and methods and, in particular, to removal of masses such as tissue and foreign matter from the bodies of humans or other animals.

BACKGROUND OF THE INVENTION

Minimally Invasive Surgery (MIS) is becoming more and more prevalent and preferred by patients. This is because MIS typically results in faster patient recovery times and shorter hospital stays, and oftentimes the procedure can be done on an outpatient basis. MIS can be in the form of endoscopic, mini-incision, robotic, or natural orifice surgery, and thus is sometimes referred to as no-scar, low-scar, bandage, keyhole, or pinhole surgery. To perform MIS the surgeon uses a variety of instruments to cut, coagulate, seal, desiccate, manipulate, denature, or otherwise work on tissue. Modern technology has effectively shrunken down the size of these devices so that they can fit through very small openings in the skin. So surgeons can insert these instruments through very small openings in the skin to devascularize and dissect a relatively large mass (such as a tumor) within the patient's body. But a problem arises when that mass will not fit through the small openings in the skin. Many skilled surgeons don't do MIS in some cases because extraction of the tissue from the patient's body would necessitate a big incision or it would take too long to de-bulk and remove the tissue.

There are known devices that are designed to de-bulk large pieces of tissue in order to remove the tissue once it is freed from the patient's body. These devices are commonly referred to as "morcellators." The first generation of morcellators consisted of a grasper with a jaw-like apparatus at the end of it. The surgeon would take small bites out of the tissue until it was totally removed.

The second (and current) generation of morcellators include a motorized tubular knife that is inserted through an opening in the body. The surgeon uses a separate instrument that inserts through the tubular knife to grab tissue and pull in into engagement with the knife, which then cuts off strips of the tissue that are then pulled through the tubular knife and discarded. This process is repeated numerous times until the entire mass of tissue is removed. But this design has many drawbacks. First of all, the motorized tubular knife is exposed so that it can engage and de-bulk the tissue, but the exposed knife can also contact and cause unintentional damage to surrounding tissue resulting in injury, hospitalization, and/or death. In addition, the tissue removal rate is dependent on the composition and stability of the tissue, the skill of the physician, the fatigue and frustration of the physician (tissue removal is typically the last step in the procedure before closing the patient), etc. Current morcellators have maximum tissue removal rates believed to be in the neighborhood of about 40-60 grams per minute. Furthermore, to effectively and safely use these devices an inert, nontoxic gas (such as carbon dioxide) must be insufflated into a body cavity to expand the cavity sufficiently to provide increased workroom and better visualization during surgery. Moreover, although current morcellating devices don't necessarily require the use of an assistant during the surgery, many surgeons find the use of the devices to be so tiresome and cumbersome that they end up using an assistant anyway.

Accordingly, it can be seen that needs exist for improvements in morcellating and removing tissue from the human body. It is to the provision of solutions meeting these and other needs that the present invention is primarily directed.

SUMMARY OF THE INVENTION

Generally described, the present invention provides a device for capturing and extracting a mass from a patient's body. The device includes a coaxial tube assembly, a bag, a bag-translating assembly, and a drive assembly. The coaxial tube assembly includes an inner tube and an outer tube that are coaxially arranged, and it has a distal end that can be positioned within the body. The inner tube defines a lumen and the outer tube cooperates with the inner tube to define an annular space. The bag receives the mass to be extracted. The bag-translating assembly includes a coupling that couples to the bag so that the distal end of the lumen of the coaxial tube assembly is surrounded by the bag. The coupling translates within the annular space of the coaxial tube assembly to move the bag from a deployed position within the body, through a retracting motion, and to a retracted position within the annular space. As the bag is moved through the retracting motion, the mass in the bag is pulled at least partially into the lumen at the distal end of the coaxial tube assembly. The drive assembly includes at least one actuator that drives the bag-translating assembly to move the bag from the deployed position to the retracted position.

In one example embodiment, the bag is mounted to the coupling in a ready position with the coupling mounted onto the inner tube and with the bag and the coupling within the annular space. In this embodiment, the drive assembly operates the bag-translating assembly to move the bag from the ready position in the annular space to the deployed position in the body. This embodiment is well suited for use in MIS with trocar/cannula systems. In an alternative example embodiment, the bag is mount to the coupling after being separately inserted into the body (e.g., through an incision or other bodily opening). This alternative embodiment is well suited for use in open surgery or in MIS using trocar/cannula systems.

In another example embodiment, the device includes a de-bulking tool that is received in the lumen of the coaxial tube assembly. In this embodiment, as the bag is moved through the retracting motion, the mass in the bag is pulled into engagement with the de-bulking tool to morcellate the mass into bits. In addition, the de-bulking tool may have a helical ridge that functions to auger and convey the mass bits through the lumen from the distal end of the coaxial tube assembly to outside of the body. In an alternative example embodiment, the device is provided without the de-bulking tool. This embodiment is well suited for use in removing masses that deform sufficiently to fit through the lumen without being de-bulked, such as fluids or small soft masses.

In typical commercial embodiments, the bag-translating assembly includes a lead-screw mechanism for converting a rotational motion of the inner tube to a linear motion of the coupling, the de-bulking tool is provided by a cutting tool with a sharp cutting head, and/or the drive assembly includes one or more rotary motors that drive the lead-screw mechanism and the cutting tool. In addition, the device may include a waste receptacle that is mounted to the coaxial tube assembly to receive the extracted mass (intact or morcellated, depending on the mass).

In other aspects, the invention provides refills for the capturing and extracting device. In typical commercial embodiments, the refills include replacement bags such as those described herein and replacement cutting tools such as those described herein.

In another aspect, the invention provides a method of extracting a mass from a patient's body. The method includes the step of inserting a distal end of a coaxial tube assembly into the body, the coaxial tube assembly having a lumen and a coaxial annular space. The method further includes the steps of inserting a bag into the body, placing the mass into the bag, and retracting the bag into the annular space through a retracting motion. As the bag is moved through the retracting motion, the mass in the bag is pulled at least partially into the lumen at the distal end of the coaxial tube assembly.

In one example method, the bag is inserted into the body through the annular space of the coaxial tube assembly. This approach is well suited for use in MIS using trocar/cannula systems. In an alternative method, the bag is inserted into the body through an opening in the body that is separate from the coaxial tube assembly. In addition, after inserting the bag into the body, the alternative method includes the step of mounting a mounting opening of the bag to the distal end of the coaxial tube assembly so that the bag encloses the distal end of the lumen. This approach is well suited for use in open surgery or in MIS with trocar/cannula systems.

In addition, the method may include the step of capturing the mass in the bag. This may be done passively by retracting a mass opening of the bag (through which the mass was inserted into the bag) into the annular space before the mass contacts the distal end of the coaxial tube assembly. Or this may be done actively by manually closing the mass opening in the bag to capture the mass in the bag.

In another example method, a de-bulking tool is inserted into the lumen of the coaxial tube assembly. In this method, as the bag is moved through the retracting motion, the mass in the bag is pulled into engagement with the de-bulking tool to morcellate the mass into bits. In addition, the de-bulking tool may have a helical ridge, and the method may further include the step of rotating the de-bulking tool to auger and convey the mass bits through the lumen from the distal end of the coaxial tube assembly to outside of the body. In an alternative method, the device is provided without the de-bulking tool and the method includes the step of extracting the mass intact through the lumen. This alternative method is well suited for use in removing masses that deform sufficiently to fit through the lumen without being de-bulked, such as fluids or small soft masses.

The specific techniques and structures employed by the invention to improve over the drawbacks of the prior devices and accomplish the advantages described herein will become apparent from the following detailed description of the example embodiments of the invention and the appended drawings and claims.

BRIEF DESCRIPTION OF THE DRAWINGS

FIG. 3A is a perspective view of the coaxial tube assembly and the bag-translating coupling of FIG. 1, showing the coupling in a position between the proximal and distal ends of the coaxial tube assembly.

FIG. 3B is a perspective view of the coaxial tube assembly and the bag-translating coupling of FIG. 3A, showing the coupling translated to a position at the distal end of the coaxial tube assembly.

FIG. 5A is a side view of the device of FIG. 1, showing the coupling in the ready position adjacent the proximal end of the coaxial tube assembly and the bag positioned within the coaxial tube assembly.

DETAILED DESCRIPTION OF EXAMPLE EMBODIMENTS

Figure 1:
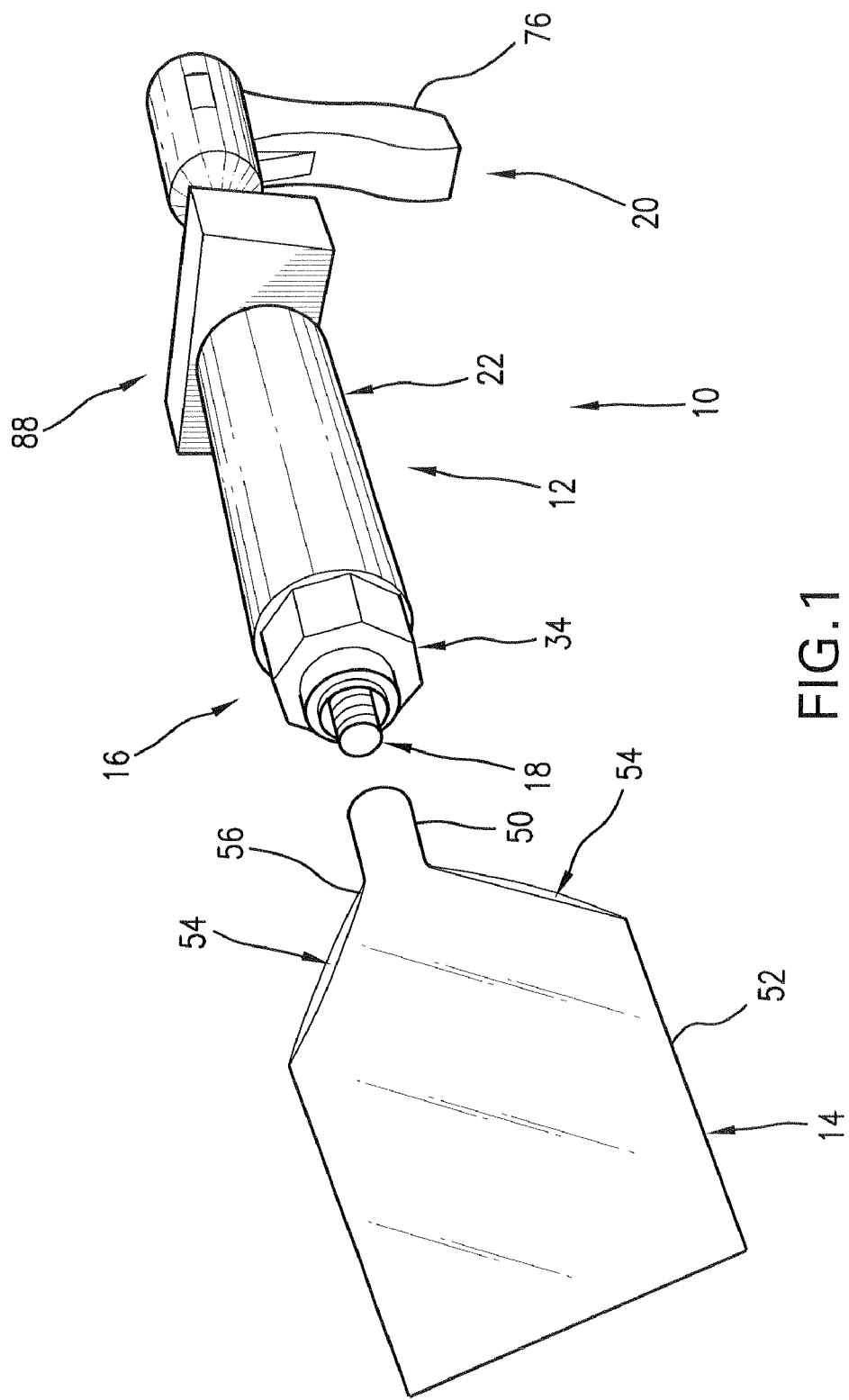
FIG. 1 is a perspective view of a tissue capture and extraction device according to a first example embodiment of the present invention, showing a coaxial tube assembly, a bag, a bag-translating assembly, a de-bulking tool, and a drive assembly.

Referring now to the drawing figures, FIGS. 1-5B show a tissue capture and extraction device 10 according to an example embodiment of the present invention. The device 10 includes a coaxial tube assembly 12, a capture bag 14, a bag-translating assembly 16, a de-bulking tool 18, and a drive assembly 20. The drive assembly 20 operates the bag-translation assembly 16 to move the bag 14 through the coaxial tube assembly 12 to deliver the bag into a cavity in a patient's body. After a mass of tissue in the cavity is freed from its surroundings and placed in the bag 14, the drive assembly 20 operates the bag-translation assembly 16 to begin retracting the bag back into the coaxial tube assembly 12. As the bag 14 is being retracted, the mass in the bag is brought into engagement with the de-bulking tool 18. Then the drive assembly 20 operates the de-bulking tool 18 to morcellate the mass in the bag 14 and extract the morcellated mass bits through the coaxial tube assembly 12. The device 10 can be adapted for de-bulking and removing most any type of mass from a human or other animal body, including human tissue, foreign bodies, bone, etc., whether in a solid and/or fluid state, and whether diseased or otherwise in need of being removed.

It will be understood that the drawings are illustrative and that, for simplicity and clarity, many of them are not to scale and that the relative proportions shown are not always accurate. For example, as shown in FIG. 1 the drive assembly 20 is disproportionately small relative to the coaxial tube assembly 12, the length of the coaxial tube assembly is disproportionately small relative to its radius, and the radial dimension of the neck of the bag 14 is disproportionately small relative to that of the coaxial tube assembly.

Figure 2:
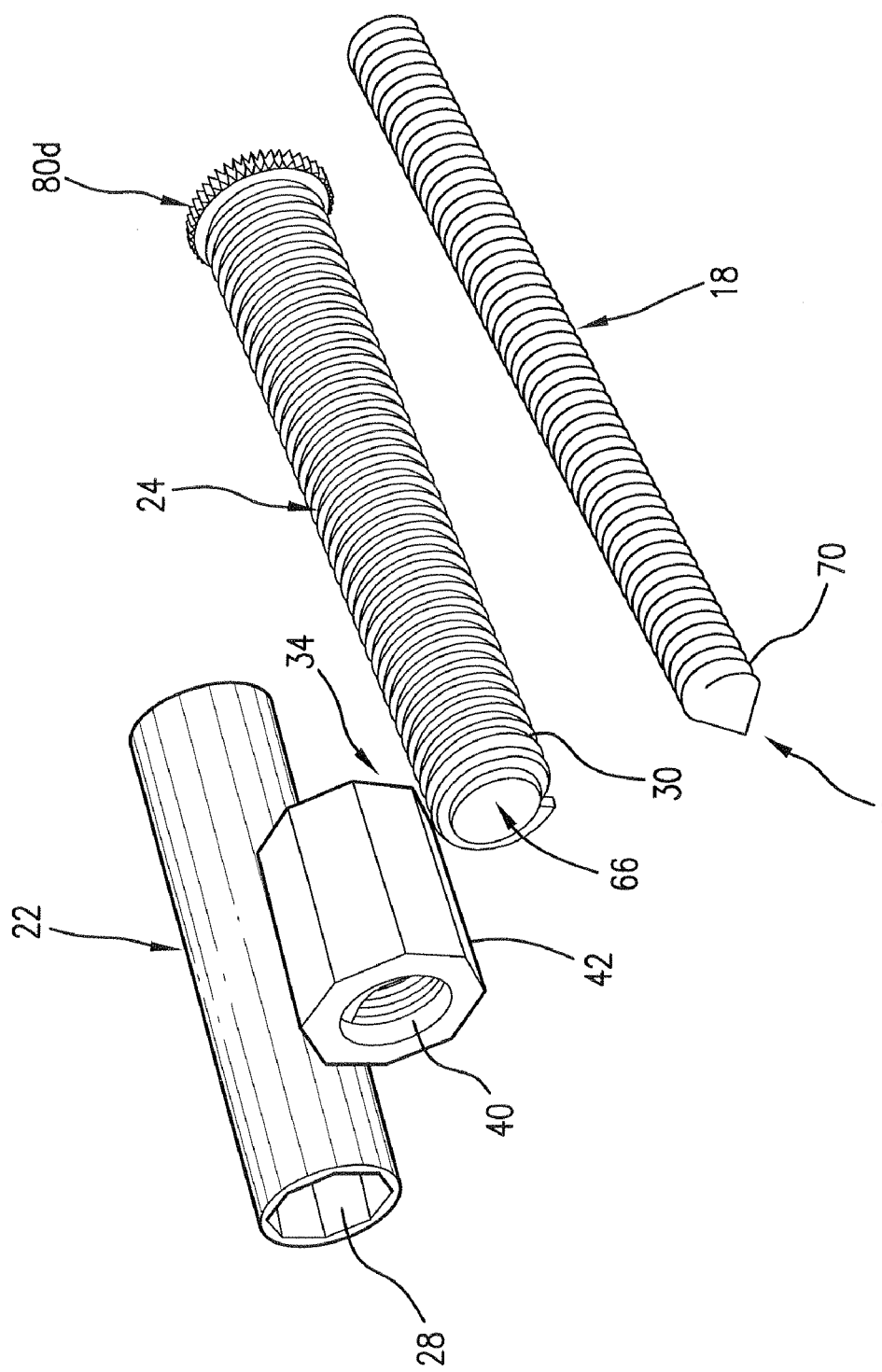
FIG. 2 is a perspective view of the de-bulking tool, the coaxial tube assembly, and a coupling of the bag-translating assembly of FIG. 1 in a disassembled state.

Referring to FIGS. 1-3, the coaxial tube assembly 12 includes an outer tube 22 and an inner tube 24 that are coaxially arranged. An inner surface 28 of the outer tube 22 has a larger radius than an outer surface 30 of the inner tube so that an annular space 32 is defined between the tubes. In a typical commercial embodiment, the outer tube 22 is cylindrical and has an outer diameter of 12 mm (so that it can be received in a 12 mm cannula), and the inner tube 24 is cylindrical and has an inner diameter of 5 mm. The coaxial tube assembly 12 functions as a delivery conduit for the capture bag 14, and the annular space 32 has a radial thickness sufficient to receive the bag in it. In addition, the inner tube 22 is hollow, the space within the inner tube defines a lumen, and the de-bulking tool 18 is received within the lumen. The coaxial tube assembly 12 also functions as an access port for the de-bulking tool 18 and a conduit for removing the morcellated mass, and the lumen has a radial thickness sufficient to receive the de-bulking tool and the morcellated bits of the mass. Furthermore, the inner tube 22 is preferably sized so that the lumen can receive other types of surgical implements commonly used in MIS.

The bag-translation assembly 16 includes a coupling 34 that is attached to the bag 14. The bag-translation assembly 16 is adapted to move the coupling 34, and thus the bag 14, through the annular space 32 of the coaxial tube assembly. The coaxial tube assembly 12 has a promixal end 36 (closest to the user) and a distal end 38 (closest to the patient), and the bag-translation assembly 16 functions to deliver the bag 14 out of the distal end of the tube assembly and into a cavity in the patient's body. In addition, the coupling 34 functions as a spacer that maintains the coaxial arrangement of the outer tube 22 and the inner tube 24. The outer tube 22, the inner tube 24, and the coupling 34 may be made of durable materials such as conventional metals and/or plastics.

In the depicted embodiment, the bag-translation assembly 16 includes a lead screw mechanism. The outer surface 30 of the inner tube 24 and the inner surface 40 of the coupling 34 have mating screw threads (e.g., progressive helical threads). And the outer surface 42 of the coupling 34 and the inner surface of the outer tube 22 have conforming non-circular profiles (such as the octagonal profiles shown) that prevent rotation between them. So upon the application of a rotational force to the inner tube 24, the coupling 34, which is constrained from rotation, linearly translates along the outer and inner tubes 22 and 24 in the annular space 32 between them.

Figure 6:
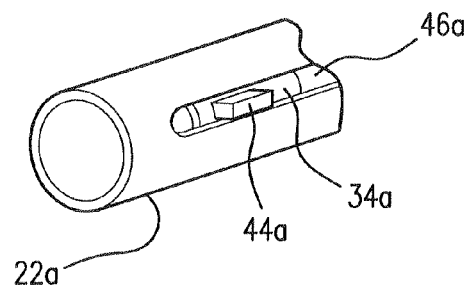
FIG. 6 is a perspective view of a portion of an alternative embodiment showing a coupling with a projection extending through a slot in an outer tube.
Figure 7:
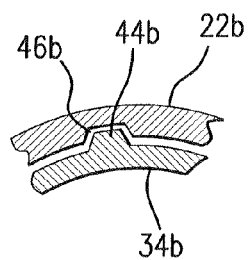
FIG. 7 is an axial cross sectional view of a portion of an alternative embodiment showing a coupling with a projection extending into a groove in an outer tube.
Figure 8:
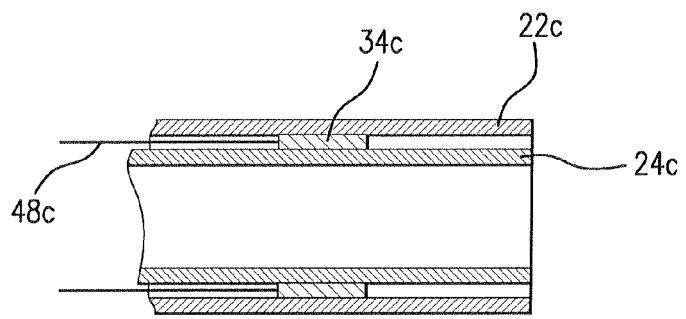
FIG. 8 is a longitudinal cross sectional view of a portion of an alternative embodiment showing a coupling that linearly slides within a coaxial tube assembly.

In alternative embodiments, the coupling and the outer tube are configured (sized and shaped) so that they nest together with a frictional interference fit that prevents (completely or at least substantially) rotation between them, instead of having the conforming non-circular profiles. In yet other alternative embodiments, the coupling and the outer tube have other conforming polygonal profiles or other regularly or irregularly shaped profiles for preventing rotation. In still other alternative embodiments, the coupling and the outer tube have two (or another number of) sets of mating key elements to prevent rotation of the coupling, instead of having the conforming non-circular profiles. For example, FIG. 6 shows the coupling 34a with protrusions (ribs, pins, tabs, etc.) 44a that are received in through-slots 46a in the outer tube 22a, and FIG. 7 shows the coupling 34b with protrusions 44b received in grooves 46b in the outer tube 22b. In yet another alternative embodiment shown in FIG. 8, instead of a lead screw mechanism, the coupling 34c slides between the outer and inner tubes 22c and 24c under pushing and a pulling forces applied (whether manual or motorized) by a rigid or semi-rigid member 48c such as an elongated plastic rod, a strip of rubber, a belt, etc. In still another alternative embodiment, instead of a lead screw mechanism, the coupling is a component of a ball-screw mechanism or another mechanism that converts rotary motion to a linear motion. And in yet still another alternative embodiment, the lead screw mechanism is configured so that rotation of the outer tube translates the coupling along the coaxial tube assembly.

Referring to FIG. 1, the capture bag 14 attaches to the coupling 34 to enclose (in cooperation with the inner tube 24) the lumen 66 at the distal end of the inner tube. In this way, the bag 14 secures and isolates the mass to be removed and, upon retraction of the coupling 34, forcibly feeds it to the inner tube lumen 66 for morcellating by the de-bulking tool 18. The bag 14 is made of a thin sheet of a material that is flexible, sufficiently non-porous that the morcellated bits of mass (as well as any fluids, diseased cells, etc. associated with the mass) will not pass through it, sufficiently durable that it will not break when subjected to the forces on it when it is pulled back into the coaxial tube assembly with the mass in it, and sufficiently inexpensive that the bag can be disposed of after one use. As such, the bag 14 may be provided by conventional soft generally non-permeable bag, by a mesh net or other woven, knit, or perforated bag, or by another structure for securing the mass and guiding it to the lumen 66.

The bag 14 has a neck portion 50, a body portion 52, and at least one mass opening 54. The neck 50 has a mounting opening for attaching to the coupling 34 by conventional fastening techniques such as, for example, a friction fit, an adhesive, a clip or clamp, etc. The mass opening 54 is sized large enough to receive through it, and the body 52 is sized large enough to receive in it, the mass that is to be removed. In the depicted embodiment, the bag 14 has two slotted mass openings 54 adjacent the proximal end 56 of the body 52 of the bag. Positioning the mass openings 54 adjacent the proximal end 56 of the bag 14 is preferable because then the openings do not need to be manually closed. This is because, when the bag 14 is retracted back into the coaxial tube assembly 12, the proximal end 56 of the bag is pulled back in first, and the mass in the bag is blocked from slipping out of the mass openings 54 once they have been pulled into the coaxial tube assembly. In this way, the mass is secured within the bag 14 in a "passive" manner, without having to manually close the openings 54.

Figure 9:
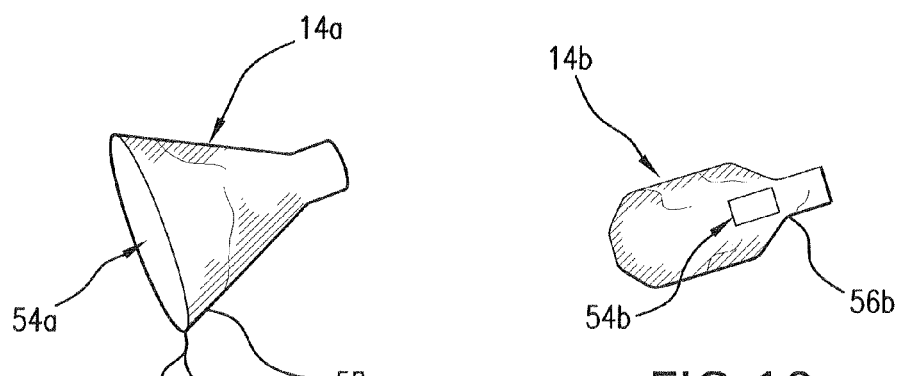
FIG. 9 is a perspective view of a bag with a distal-end opening according to an alternative embodiment.
Figure 10:
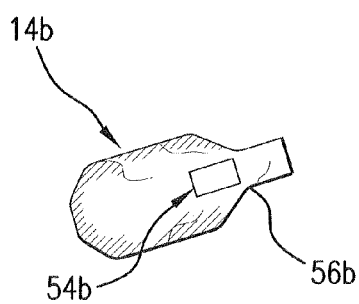
FIG. 10 is a perspective view of a bag with a proximal-end opening according to an alternative embodiment.

In an alternative embodiment shown in FIG. 9, the bag 14a has one mass opening 54a at its distal end 58a and a closure 60a (a drawstring, collapsible hoop, reopening tie, non-reopening tie, etc.) for closing the opening after the mass has been placed inside the bag. The closure 60a is manually operated (i.e., in an "active" manner) to close the mass opening 54a by a separate surgical implement inserted into the bodily cavity through a separate or the same cannula or incision in the body. In addition, with the distal mass opening 54a opened, the bag 14a can be wrapped around the inner tube 24 with the inner tube extending through the distal mass opening, so other surgical tools can be inserted through the lumen 66 and into the body cavity before deploying the bag. In another alternative embodiment that is shown in FIG. 10, the bag 14b has one mass opening 54b at its proximal end 56b. In an alternative embodiment that is similar to those shown in FIGS. 9 and 10, the bag has one mass opening and a closure at its distal end as well as three (or another number of) mass openings adjacent its proximal end. In this embodiment, the distal mass opening can be closed by the closure and a mass can be inserted into the bag through one of the proximal mass openings, or a mass can be inserted into the bag through the distal mass opening and then the opening closed, so the surgeon can use the same style of bag for inserting the mass in the distal or proximal end of the bag. In other alternative embodiments, the bag has a conical, polygonal, or other regular or irregular shape and/or has more than two mass openings. And in still other alternative embodiments, the bag is made of a material that is sufficiently non-porous that bodily fluids will not pass through it.

Figure 11A:
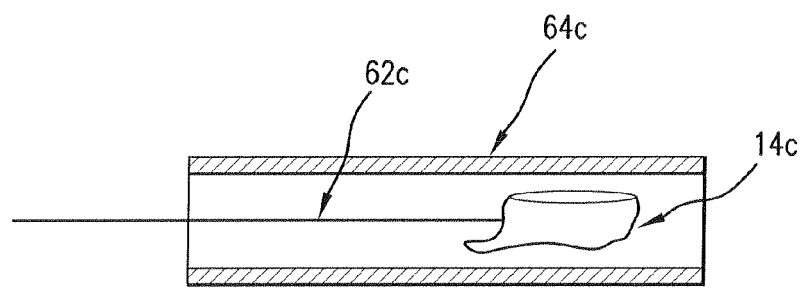
FIG. 11A is a side view of a bag with a handle according to an alternative embodiment, showing the bag being inserted through a cannula.
Figure 11B:
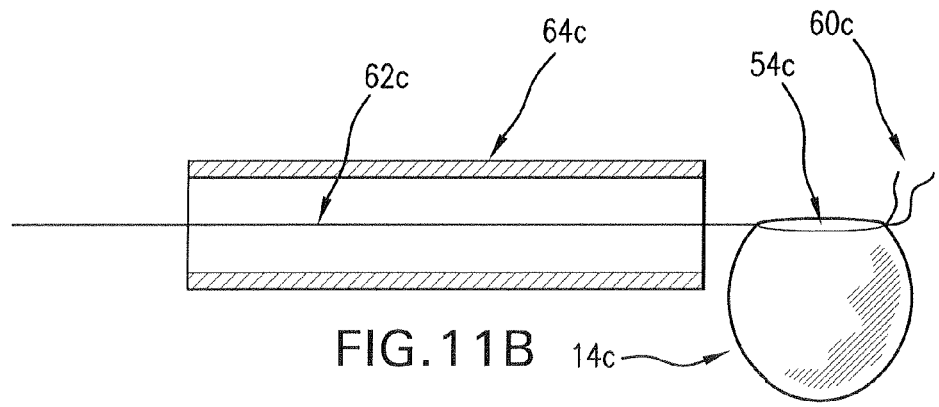
FIG. 11B is a side view of the bag and cannula of FIG. 11A, showing the bag extended out of the cannula.
Figure 12:
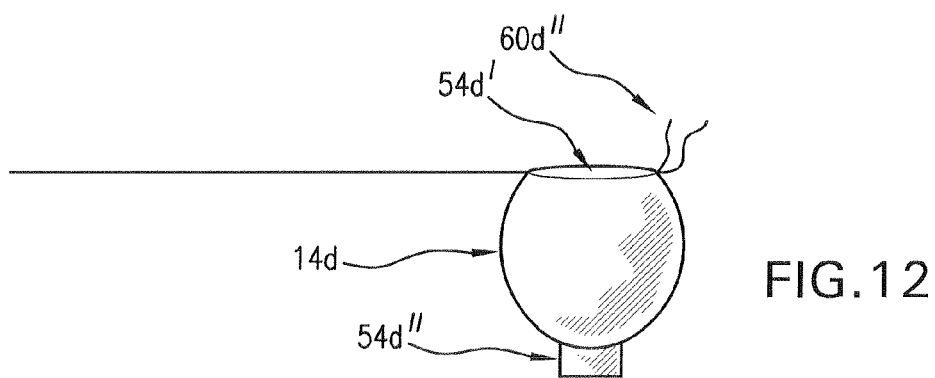
FIG. 12 is a side view of a bag with a handle and two openings according to an alternative embodiment.

In addition, in other alternative embodiments of the invention, the bag is not initially attached to the coupling, and instead the bag is inserted into the patient's body separately (e.g., through a secondary cannula or an incision in open surgery) and loaded with the mass to be extracted, and then the mass-laden bag is attached to the device for morcellation and extraction. For example, FIGS. 11A and 11B show an alternative embodiment in which the bag 14c has an elongated handle 62c and is inserted through a secondary cannula 64c into the patient's body. The bag 14c has a combination mounting/mass opening 54c and a closure 60c. The mass is loaded through the combination mounting/mass opening 54c and into the bag 14c, the opening is fitted onto the coupling, and the closure 60c is actuated to close the opening and secure the bag in place on the coupling. The bag 14c can be attached to the coupling within the body cavity, or the bag can be moved so that the opening 54c is outside of the body (with most of the bag and the mass still within the cavity) and the coupling attached there. In a similar alternative embodiment shown in FIG. 12, the bag 14d has two openings 54d' and 54d" and two closures 60d' and 60d". The mass is loaded through the mass opening 54d" and into the bag 14d, the first closure 60d' is actuated to close the first opening, and the mounting opening 54d" is positioned over the coupling (an attachment may be provided for securing the bag in place on the coupling).

Referring back to FIGS. 1 and 2, the de-bulking tool 18 is sized to be received in the lumen 66 of the coaxial tube assembly 12. Preferably, the cutting tool 18 is removably received in the lumen 66. In the depicted embodiment, the de-bulking tool 18 is provided by an elongated cutting tool with a sharp cutting head 68 at its distal end for morcellating the mass to be extracted. The cutting head 68 of the de-bulking tool 18 is positioned at the distal end 38 of the coaxial tube assembly 16 so that when the bag 14 is retracted the mass in the bag is forced into engagement with the cutting head. For safety, the cutting head 68 is preferably positioned slightly within the distal end 38 of the coaxial tube assembly 16 and extends no more than about 1/16-1/4 inch out of the distal end. In addition, the cutting tool 18 preferably has a helical ridge 70 that produces an augering action when the cutting tool is rotated, and the ridge extends along at least the portion of its length that is within the lumen 66. In this way, the helical ridge 70 conveys the morcellated bits from the distal end 38 of the coaxial tube assembly 12, through the lumen 66, and out of the proximal end 36. The cutting tool 18 may be made of a metal or other conventional material, and may be provided as a disposable or reuseable item. In a typical commercial embodiment, the cutting tool 18 is provided by a conventional 1/4-inch auger drill bit.

Figure 13A:
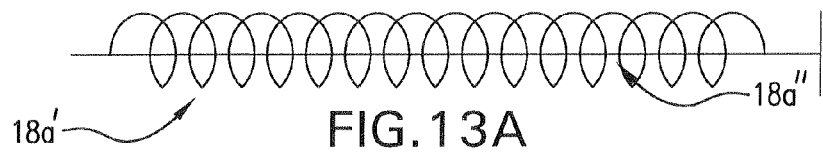
FIG. 13A is a side view of two coaxial cutting tools according to an alternative embodiment.
Figure 13B:
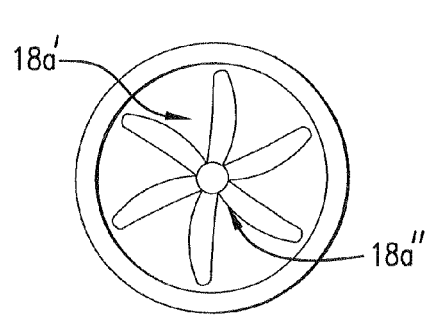
FIG. 13B is an end view of the cutting tools of FIG. 13A.
Figure 14B:
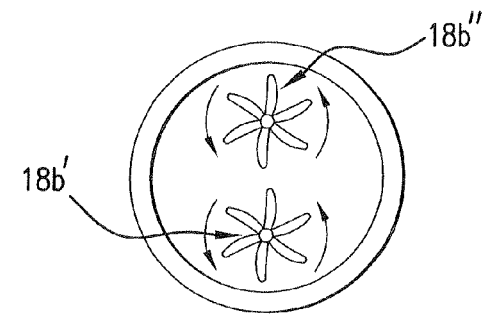
FIG. 14B is an end view of the cutting tools of FIG. 14A.
Figure 14A:
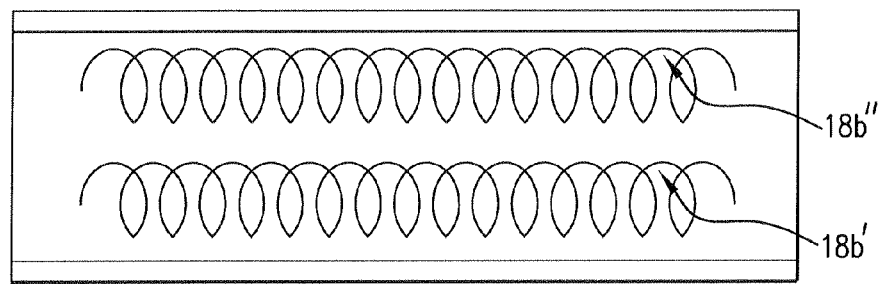
FIG. 14A is a side view of two parallel cutting tools according to an alternative embodiment.
Figure 15A:
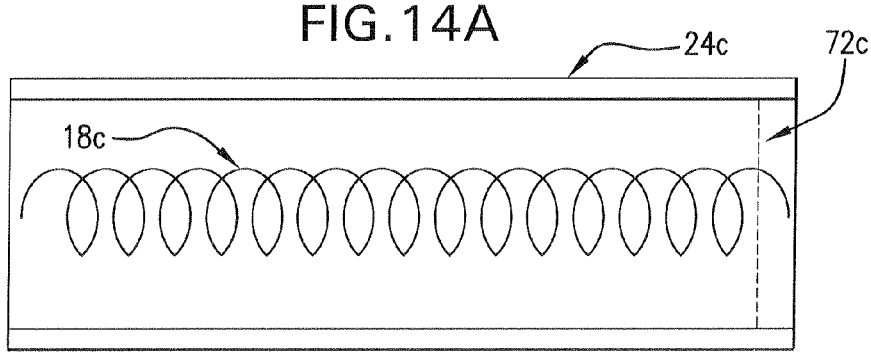
FIG. 15A is a side view of a cutting tool and a fixed member of an inner tube according to an alternative embodiment.
Figure 15B:
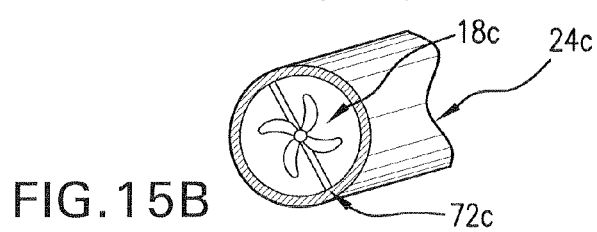
FIG. 15B is a perspective view of the cutting tool and tube of FIG. 15A.
Figures 16A, 16B:
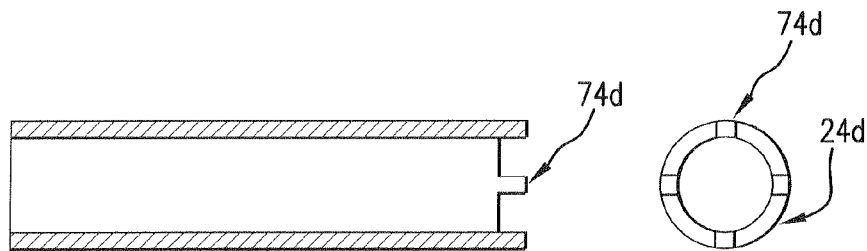
FIG. 16A is a side view of an outer tube with end projections according to an alternative embodiment.
FIG. 16B is an end view of the outer tube of FIG. 16A.

In alternative embodiments, the device 10 includes two cutting tools that rotate in opposite directions within the inner tube so that the torsional forces generated the cutting tools generally counteract each other. Such multi-cutting-tool embodiments produce a higher throughput and are well suited for removing particularly large masses. For example, FIGS. 13A-13B show an alternative embodiment with two coaxial cutting tools 18a' and 18a". And FIGS. 14A-14B show an alternative embodiment with two parallel cutting tools 18b' and 18b". In another alternative embodiment shown in FIGS. 15A-15B, the distal end of the inner tube 24c includes a fixed member 72c that cooperates with the cutting tool 18c (the cutting head shears relative to the fixed member) to reduce the torsional forces transmitted to the tissue mass. In yet another alternative embodiment shown in FIGS. 16A-16B, the distal end of the inner tube 24c includes projections 74d (one or more teeth, tines, tabs, fingers, etc., or a roughened surface) that stabilize the tissue mass during de-bulking morcellation so that it is less likely to spin. In other alternative embodiments, the distal end of the inner tube (or a third tube coaxially arranged within the inner tube and operably coupled to a pressure-activated mechanism) includes sharpened projections (one or more teeth, tines, tabs, fingers, etc.) or a sharpened edge that cuts/morcellates the tissue mass. In still other alternative embodiments, the cutting tool is provided by a conventional mechanical cutting tool other than a drill bit, for example, a small knife blade, a sharp claw, etc. In other alternative embodiments, the cutting tool does not include the helical ridge and the morcellated bits are forced through the coaxial tube assembly as the device 10 is pushed against the mass. In yet other alternative embodiments, the de-bulking tool is not provided by a cutting tool but instead is provided by another type of implement for de-bulking tissue, such conventional devices that de-bulk by the use of bipolar energy, harmonic energy, etc. And in alternative embodiments for use in extracting fluid masses or masses that are sufficiently deformable that they can be forced through the lumen of the inner tube without being morcellated, the device is provided without a de-bulking tool. Instead, a grasping tool can be inserted through the lumen to grasp and pull out the mass, a suction head can be inserted through the lumen to draw out the mass, or the mass can be forced into the lumen merely by the force of the bag being retracted.

Referring back to FIGS. 1 and 5A-5B, the drive assembly 20 operably couples to and drives the bag-translation assembly 16 and the de-bulking tool 18. The drive assembly 20 drives the inner tube 24 in a first rotary direction so that the coupling 34 translates along the inner tube from a ready position, in a direction toward the distal end 38 of the coaxial tube assembly 12, and to a deployed position to deliver the bag 14 out of the distal end. The drive assembly 20 also drives the inner tube 24 in a second opposite rotary direction so that the coupling 34 translates in the opposite direction to a retracted position to retract the bag 14 back into the distal end 38 of the coaxial tube assembly 12. And the drive assembly 20 drives the de-bulking tool 18 to morcellate the mass that has been placed into the bag 14 as the bag is retracted. So the de-bulking tool 18 is configured so that it morcellates and augers when it rotates in the second rotary direction.

The drive assembly 20 includes at least one actuator 76 for driving the bag-translation assembly 16 and/or the de-bulking tool 18. The actuator 76 may be an electric rotary motor with an internal power source (e.g., batteries) or a cord for connecting to an external power source. Preferably, the actuator 76 is handheld and portable, like a portable hand drill. The actuator 76 may be provided as a disposable or reuseable item. In addition, the drive assembly 20 includes conventional controls such as an on/off control, a rotary speed control, a rotation direction control, etc.

In the depicted embodiment, the same actuator 76 drives the bag-translation assembly 16 and the de-bulking tool 18. The de-bulking tool 18 is coupled directly to the drive shaft 82a of the actuator 76. And the drive assembly 20 includes a linkage mechanism such as a gear-set 78 operably coupling the inner tube 24 to the actuator 76. For example, the gear-set 78 may include first and second meshed gears 80a and 80b, third and fourth meshed gears 80c and 80d, and a second drive shaft 82b. The first gear 80a is coaxially mounted to the drive shaft 82a of the actuator 76, the fourth gear 80d is coaxially mounted to the inner tube 24 (see also FIG. 2), and the second and third gears 80b and 80c are connected by the second drive shaft 82b. The fourth gear 80d has a center-hole through which the de-bulking tool 18 extends freely so that the rotary motion of the de-bulking tool is not restricted. In this way, the same actuator 76 can be activated to rotate the inner tube 24 and the de-bulking tool 18 to perform their intended functions. The de-bulking tool 18 will be rotated while the bag-translating assembly 16 is being operated to deploy the bag 14, of course, but this does not impact the effectiveness of the device 10.

Figure 17A:
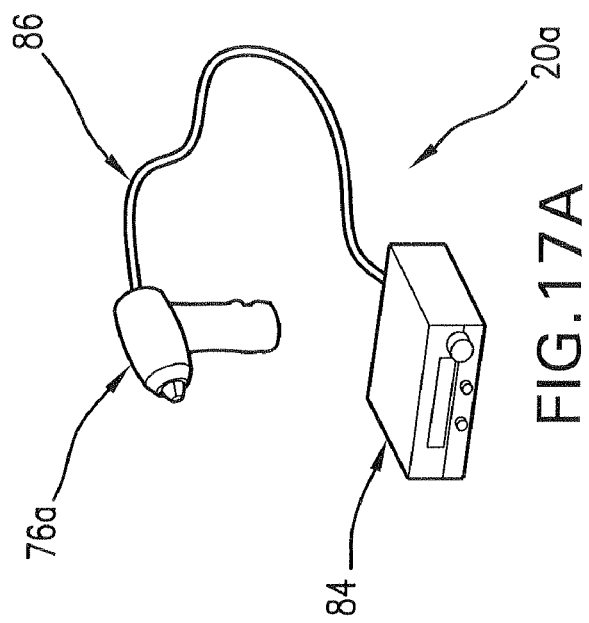
FIG. 17A is a perspective view of a controller coupled to a rotation-transmitting cable which in turn is coupled to a portable handle device according to an alternative embodiment.
Figure 17B:
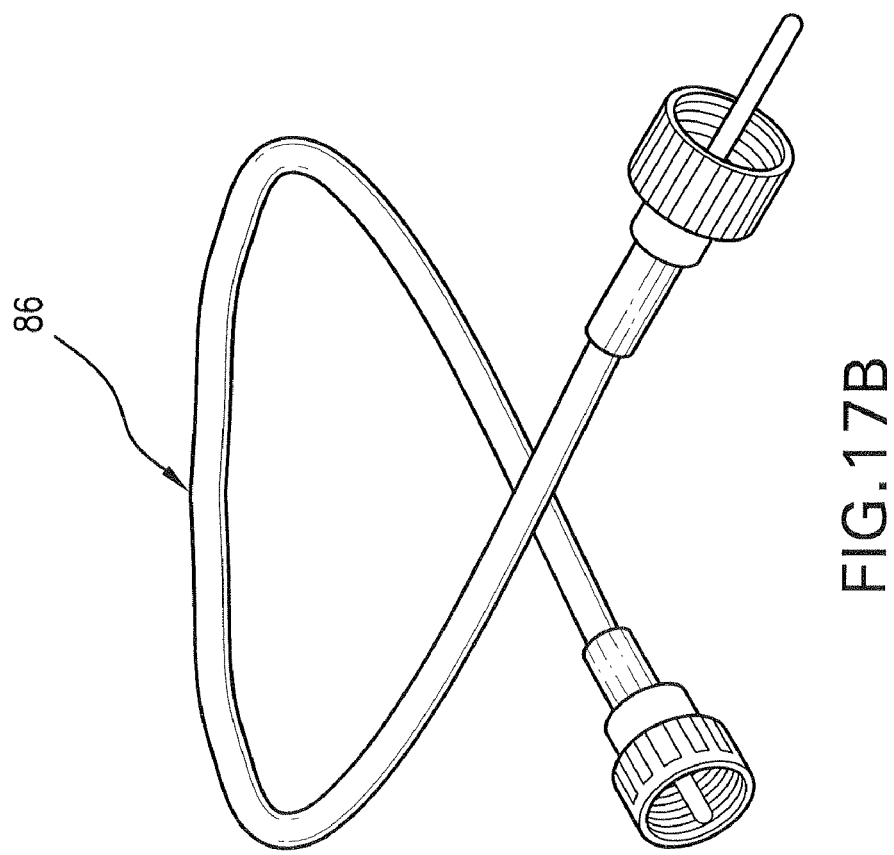
FIG. 17B is a perspective view of the rotation-transmitting cable of FIG. 17A.

In alternative embodiments, the drive assembly 20 has dedicated actuators for the bag-translation assembly and the de-bulking tool. Such embodiments may still include a gear-set or other mechanical linkage to offset the drive axis of the de-bulking tool or the inner tube. In the alternative embodiment shown in FIG. 17A, the drive assembly 20 includes a controller device 84 housing a motor (not shown) that is operably coupled by a conventional rotation-transmitting cable 86 to a lightweight handle device 76a (which does not include a motor), which in turn can be operably coupled to the de-bulking tool and the inner tube. In other alternative embodiments, the drive assembly 20 includes a controller device housing two motors that are operably coupled by conventional rotation-transmitting cables to two lightweight handle devices, which in turn are operably coupled to the de-bulking tool and the inner tube. In yet other alternative embodiments, the drive assembly has other linkage mechanisms such as chains, belts, etc., or sprockets, bevel gearing, or other types of gear-sets, for permitting the same actuator to drive both the inner tube and the de-bulking tool. And in still other alternative embodiments, the drive assembly includes a pressure-activated mechanism (e.g., a pressure-sensitive switch, a friction plate (i.e., a clutch)) operably connected to the actuator for the de-bulking tool so that the de-bulking tool is automatically activated when the mass is forced (by the bag being retracted) into contact with the de-bulking tool (or the inner tube or a trigger of the pressure-activated mechanism itself) to close the switch.

In addition, the device 10 preferably includes a waste receptacle 88 that receives the morcellated bits of mass extracted by the de-bulking tool 18. In the depicted embodiment, the receptacle 88 has an opening that is mounted adjacent the proximal end 38 of the coaxial tube assembly 12 so that as the morcellated bits are conveyed out of the proximal end they are deposited into the receptacle. The receptacle 88 has a size selected for the mass to be removed, may be provided in most any shape, and may be made of a material commonly used in medical devices. In the depicted embodiment, the gear-set 78 of the drive assembly 20 is located within the waste receptacle 88, though it could be positioned elsewhere.

Figure 4A:
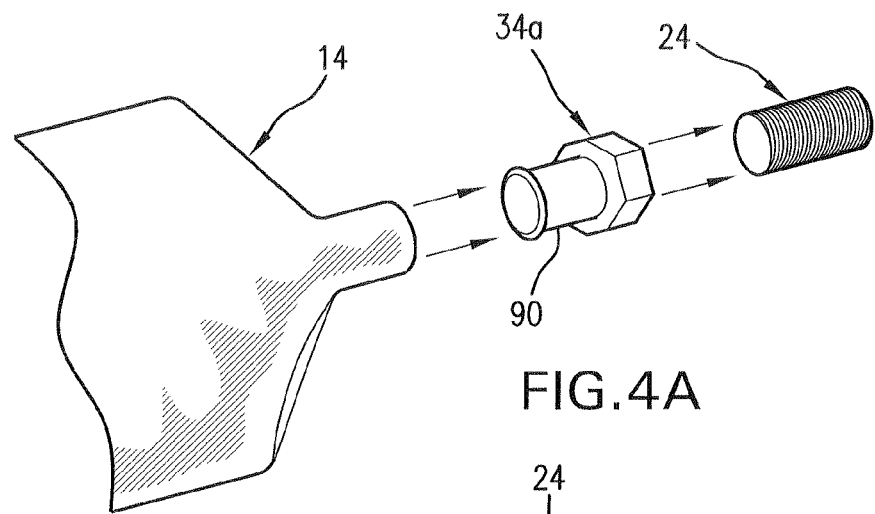
FIG. 4A is an exploded perspective view of the neck end of the bag, the bag-translating coupling, and the distal end of an inner tube of the coaxial tube assembly of FIG. 1.
Figure 4B:
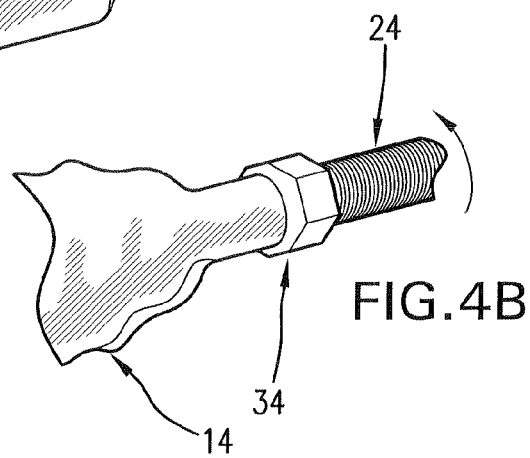
FIG. 4B is a perspective view of the bag, the coupling, and the inner tube of FIG. 4A, showing the bag mounted onto the coupling and the coupling being mounted onto the inner tube.
Figure 4C:
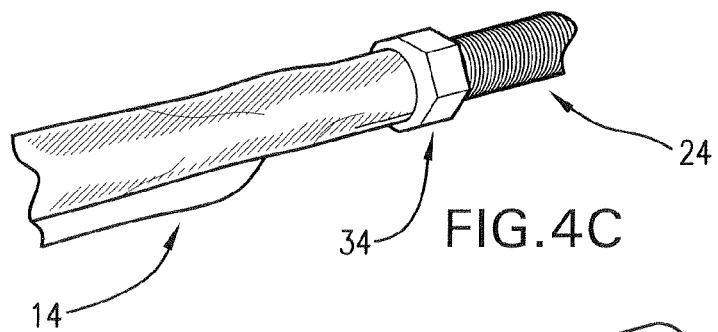
FIG. 4C is a perspective view of the bag, the coupling, and the inner tube of FIG. 4B, showing the bag wrapped around the inner tube.
Figure 4D:
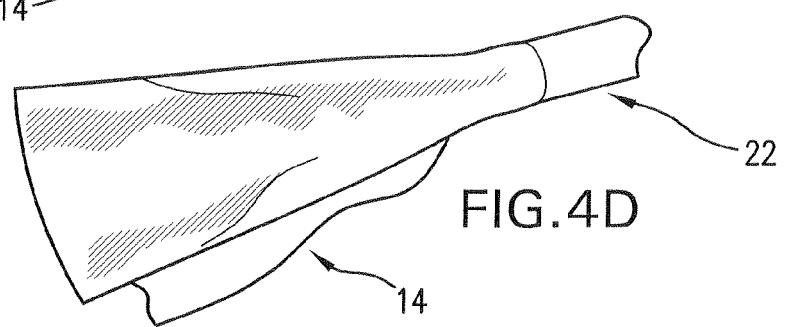
FIG. 4D is a perspective view of the bag/coupling/inner tube assembly of FIG. 4C being inserted into an outer tube of the coaxial tube assembly.
Figure 5B:
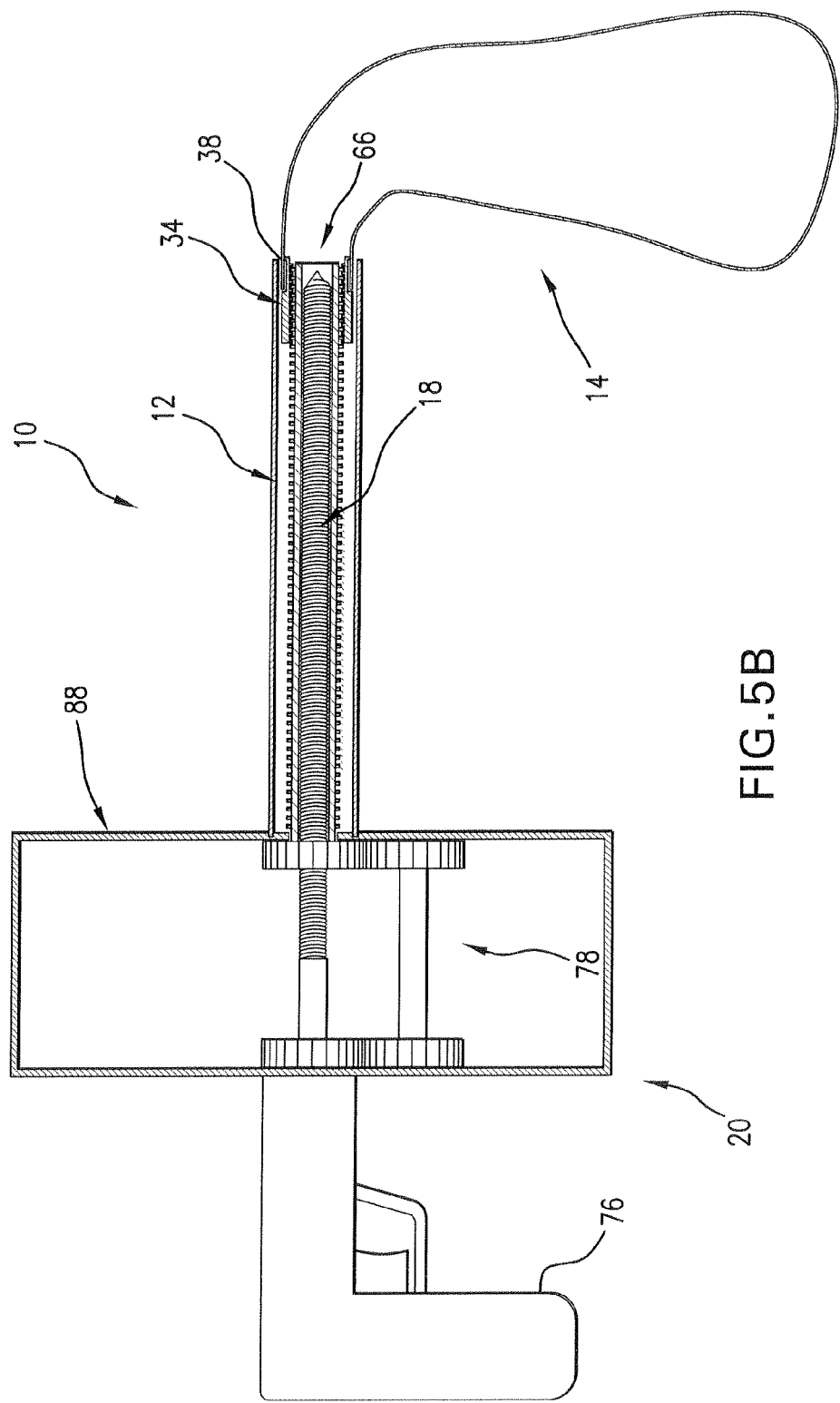
FIG. 5B is a side view of the device of FIG. 5A, showing the coupling in the deployed position adjacent the distal end of the coaxial tube assembly and the bag delivered out of the coaxial tube assembly.

FIGS. 4A-4D show how the bag 14 is loaded into the coaxial tube assembly 12. As shown in FIG. 4A, the bag 14 is mounted to the coupling 34a and the coupling is mounted to the inner tube 24. FIGS. 4A-4C show an alternative coupling 34a that includes a sleeve 90 onto which the neck of the bag 14 is secured. As shown in FIG. 4B, the coupling 34a and the inner tube 24 are rotated (as indicated by the directional arrow) relative to each other until the coupling is advanced to the proximal end of the inner tube. As shown in FIG. 4C, the bag 14 is then wrapped around the inner tube 24 or otherwise displaced into a compact arrangement. As shown in FIG. 4D, the bag/inner tube/coupling assembly 14/34/24 of FIG. 4C is then inserted into the outer tube 22. If the de-bulking tool 18 is being used, it can be inserted through the lumen 66 of the inner tube 24. The inner tube 24 and the de-bulking tool 18 are then coupled to the drive assembly 20 and the device is now ready for use.

Referring now to FIGS. 18A-18J, a method of capturing and extracting tissue masses from bodies will now be described. The method can be carried out using any of the devices described herein or using other similar medical devices. For clarity, the method is described below in conjunction with the use of the device 10 described above.

Figure 18A:
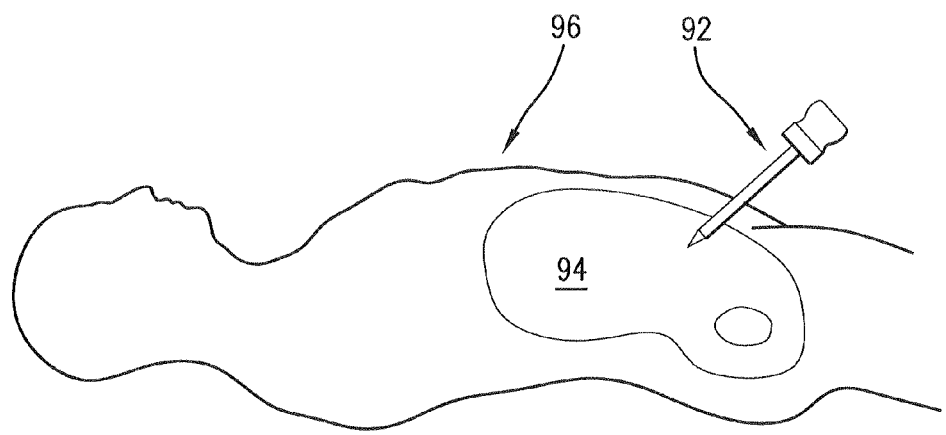
FIG. 18A is a side view of a patient's body, showing a trocar/cannula inserted in the body according to a surgical method of the present invention.
Figure 18B:
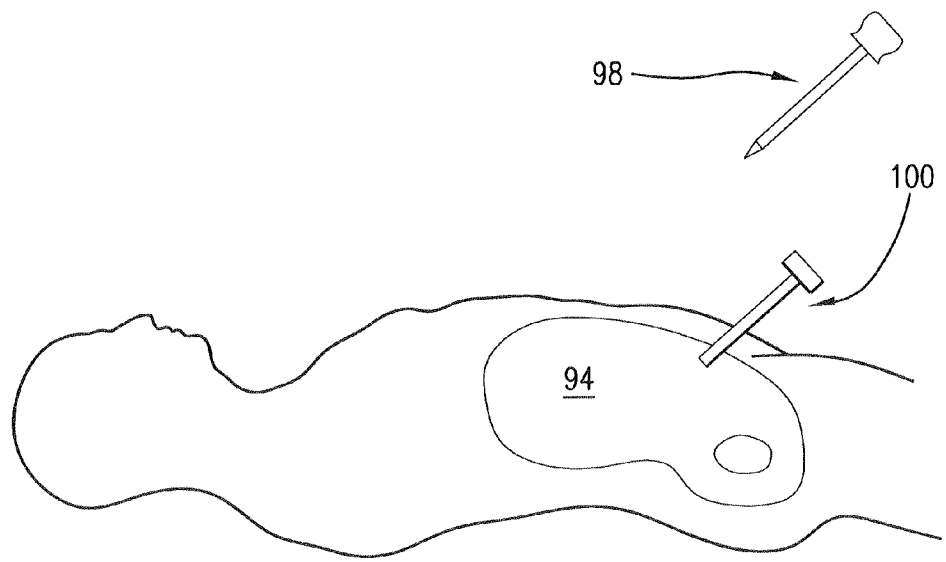
FIG. 18B is a side view of the body of FIG. 18A, showing the trocar being removed.
Figure 18C:
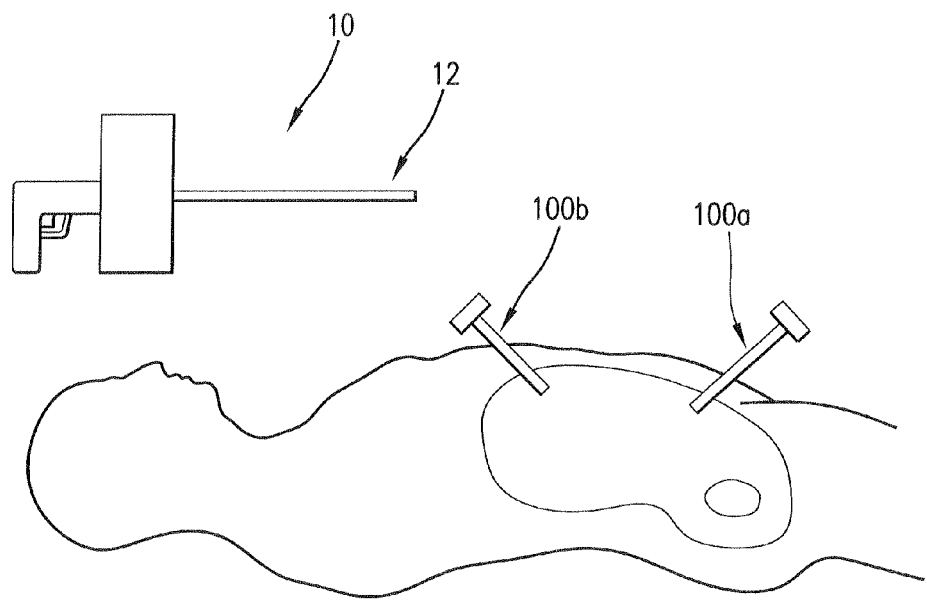
FIG. 18C is a side view of the body of FIG. 18B, showing a second cannula inserted.

To perform the method, a surgeon inserts the leading end of a conventional trocar/cannula system 92 into a cavity 94 of a patient's body 96, as shown in FIG. 18A. The cavity 94 may be natural (pre-existing) or artificial (formed by the surgeon). Then the surgeon removes the trocar 98 from the cannula 100, leaving the cannula behind, as shown in FIG. 18B. The cannula 100 is the port that is used for instrumentation in endoscopic surgery. Typically, there are two to four cannulae used in a procedure, so the above steps are repeated as necessary. In FIG. 18C, for example, there are two cannulae 100a and 100b shown.

Figure 18D:
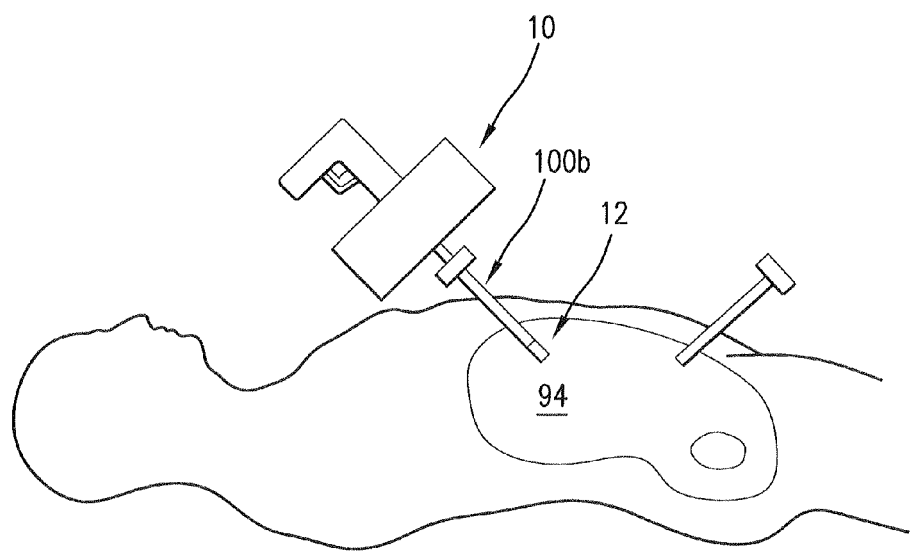
FIG. 18D is a side view of the body of FIG. 18C, showing a coaxial tube assembly of a tissue capture and extraction device inserted through the second cannula.
Figure 18E:
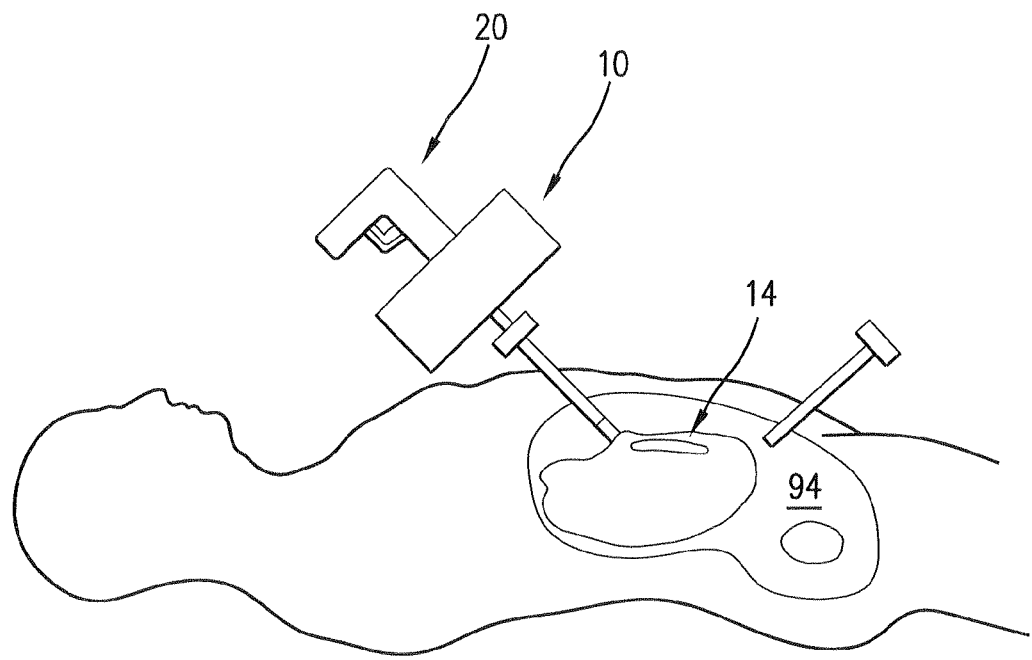
FIG. 18E is a side view of the body of FIG. 18D, showing the device operated to deploy a bag into a cavity in the body.
Figure 18F:
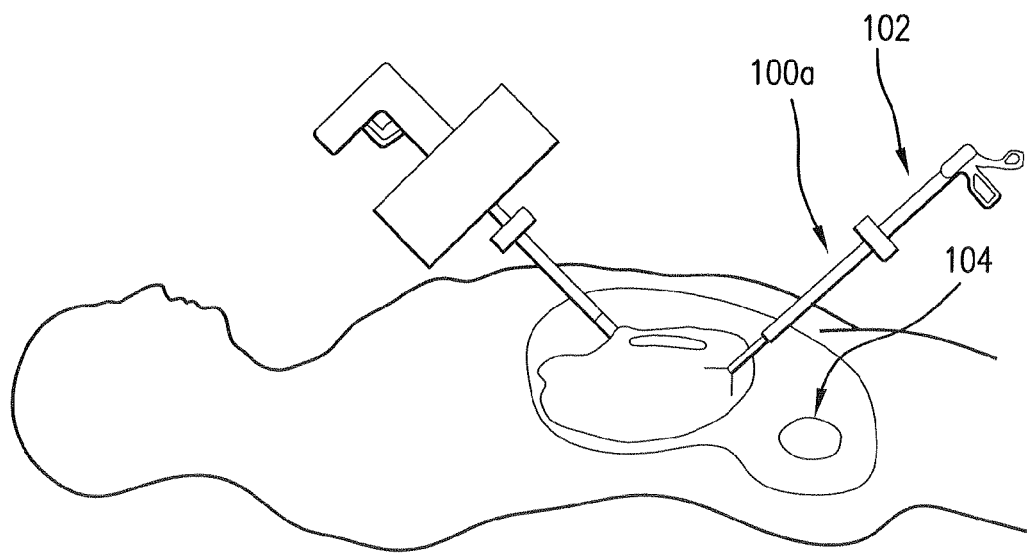
FIG. 18F is a side view of the body of FIG. 18E, showing a grasping device inserted through the first cannula.
Figure 18G:
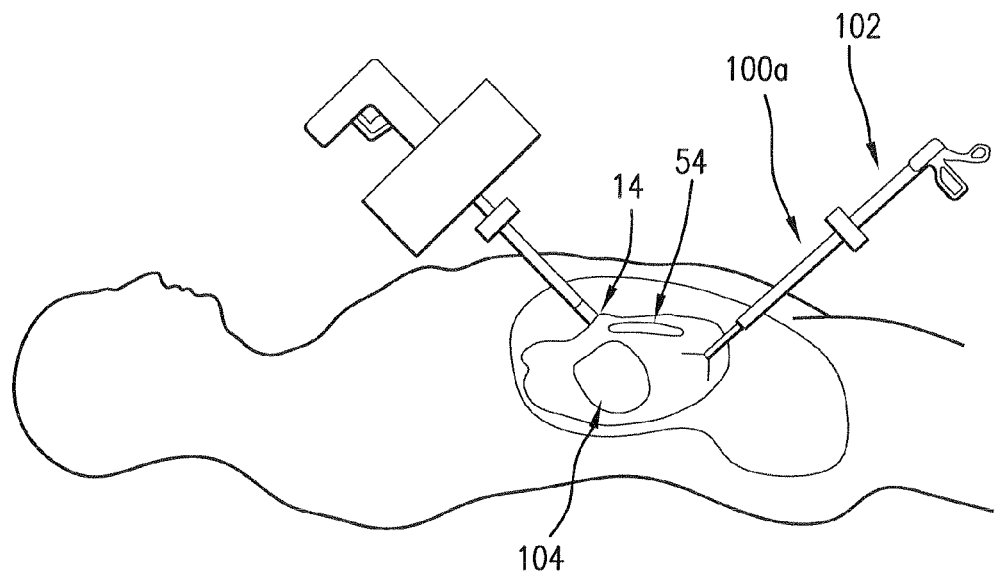
FIG. 18G is a side view of the body of FIG. 18F, showing the grasping device used to move a tissue mass into the bag.
Figure 18H:
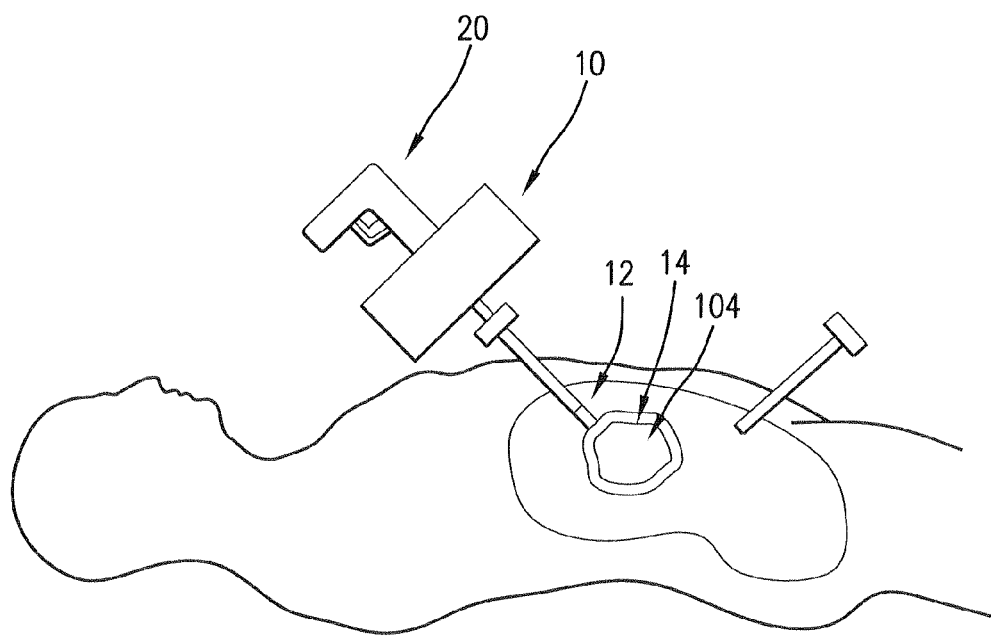
FIG. 18H is a side view of the body of FIG. 18G, showing the device operated to retract the bag.
Figure 18I:
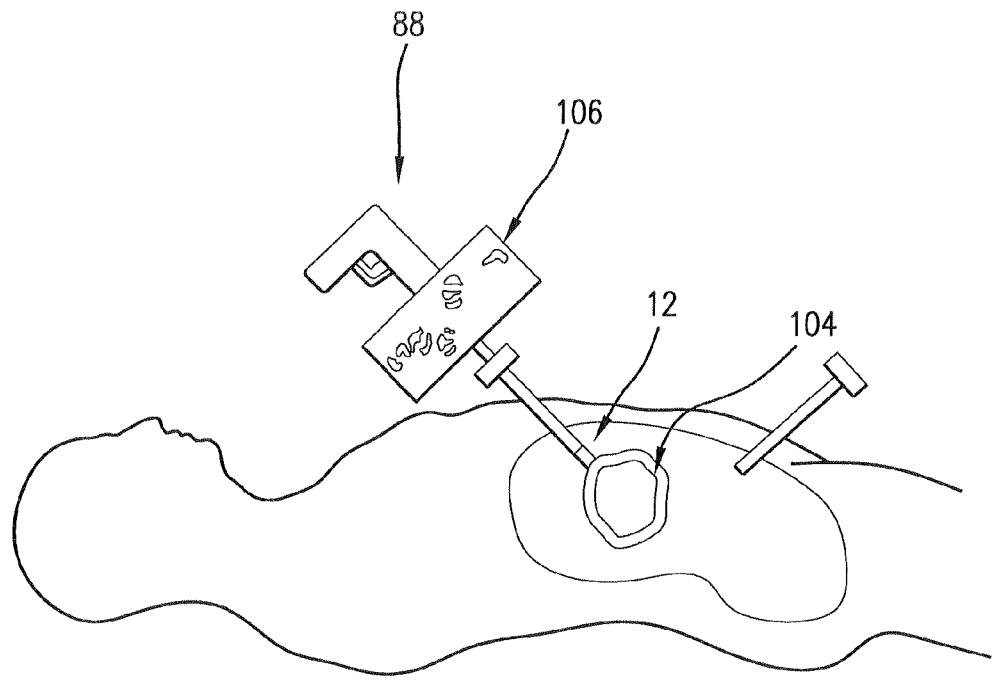
FIG. 18I is a side view of the body of FIG. 18H, showing the device further operated to further retract the bag so that the mass engages a de-bulking tool that morcellates the mass into bits.
Figure 18J:
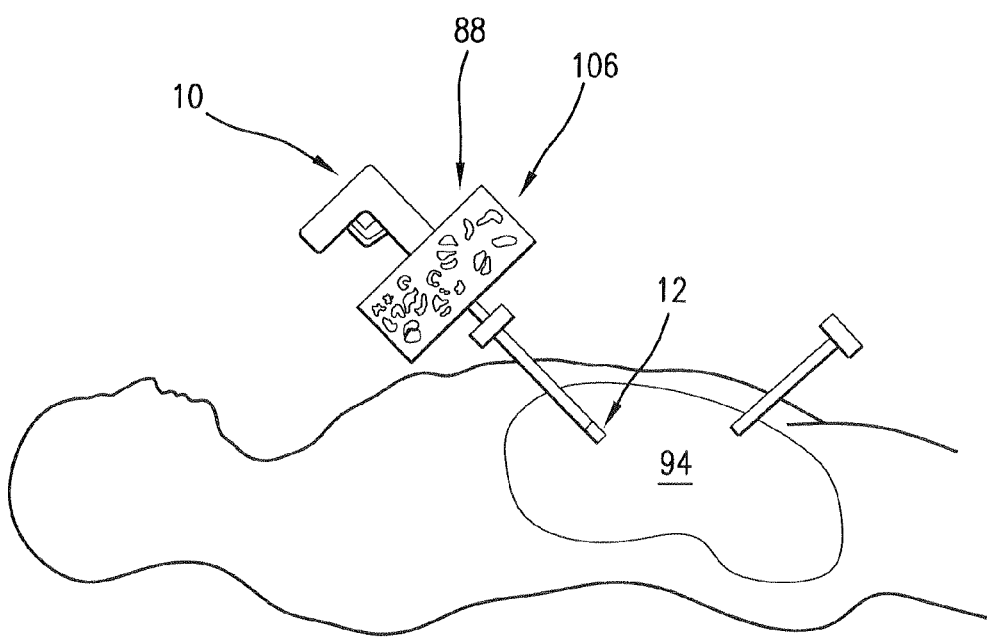
FIG. 18J is a side view of the body of FIG. 18I, showing the device further operated to fully retract the bag so that all of the mass has been morcellated into bits and conveyed out of the cavity through the device.

Next the surgeon inserts the coaxial tube assembly 12 of the device 10 through the second cannula 100b, as shown in FIG. 18D. Then the surgeon activates the drive assembly 20 to convey the capture bag 14 into the cavity 94, as shown in FIG. 18E. If the surgeon hasn't already done so, she now inserts a conventional dissecting tool through the first cannula 100a, frees the mass 104 from the surrounding tissue, and removes the cutting tool. Next the surgeon inserts a grasping tool 102 through the first cannula 100a, as shown in FIG. 18F. Then the surgeon manipulates the grasping tool 102 to grasp the mass 104 and move it through the bag opening 54 and into the bag 14, as shown in FIG. 18G. Next the surgeon operates the drive assembly 20 to retract the bag 14 through a retracting motion back into the coaxial tube assembly 12 and to activate the de-bulking tool 18, as shown in FIGS. 18H-18J. As the bag 14 is retracted, the bag opening 54 is pulled into the coaxial tube assembly 12, as shown in FIG. 18H, so there is practically no chance of any of the mass escaping the bag. As the bag 14 is retracted further, the mass 104 is pulled into engagement with the de-bulking tool 18, which morcellates the mass into smaller bits 106 and conveys the bits through the lumen 66 of the coaxial tube assembly 12 and into the waste receptacle 88, as shown in FIG. 18I. And when the bag 14 is retracted all the way back into the coaxial tube assembly 12, all of the mass has been de-bulked and conveyed into the waste receptacle 88, as shown in FIG. 18J. To complete the procedure, the surgeon turns off the device 10 and removes it from the cannula 100b, and removes the cannulae 100a and 100b.

It will be understood that the method can be carried in other variations. For example, in cases where the mass to be extracted is a fluid or soft mass that can be forced through the lumen of the inner tube without being de-bulked, the method does not include the step of activating a de-bulking tool. In addition, in cases where a bag is provided that attaches to the device intra-operably (see, e.g., FIGS. 10-12), the method includes the step of inserting the bag through a cannula (other than the cannula for the device) or another opening in the body, loading the mass into the bag, and attaching the bag to the coupling. Furthermore, the method can be carried out using trocar/cannula systems or other natural or surgically made openings in the body.

Furthermore, the method can be adapted for use in "open" surgery, with the trocar and cannula systems eliminated and instead using an incised larger opening in the patient's skin. In such open surgeries, the bag can be inserted through the coaxial tube assembly or it can be separately inserted into the cavity through the incised larger opening, loaded with the mass to be removed, and attached to the device for mass morcellation. The distal end of the coaxial tube assembly can be inserted through the incised larger opening and the bag attached to it there, or it can be positioned just outside of the body and the bag pulled out slightly through the incised larger opening and attached to it there. In this way, the device can be used with a larger-capacity bag to remove much larger masses through an incision that is too small (e.g., about 20-40 mm) to remove the intact mass through.

Accordingly, it can be seen that the present invention provides numerous advantages over known morcellators. Advantageously, the morcellation of the mass into bits and the extraction of those bits is done automatically and at a much higher rate. In addition, the mass to be extracted is captured and de-bulked in a bag, so bits of the mass are not dispersed about the cavity, eliminating later clean-up time and effort and ensuring that no diseased mass bits are left behind. Furthermore, the morcellating head of the de-bulking tool remains within (or only slightly extended out of) the device and within the bag, so there is little risk of accidentally damaging tissue other than the mass to be extracted, and the bodily cavity does not need to be insufflated to use the device to remove the mass.

It is to be understood that this invention is not limited to the specific devices, methods, conditions, or parameters described and/or shown herein, and that the terminology used herein is for the purpose of describing particular embodiments by way of example only. Thus, the terminology is intended to be broadly construed and is not intended to be limiting of the claimed invention. For example, as used in the specification including the appended claims, the singular forms "a," "an," and "the" include the plural, the term "or" means "and/or," and reference to a particular numerical value includes at least that particular value, unless the context clearly dictates otherwise. In addition, any methods described herein are not intended to be limited to the sequence of steps described but can be carried out in other sequences, unless expressly stated otherwise herein.

While the invention has been shown and described in example forms, it will be apparent to those skilled in the art that many modifications, additions, and deletions can be made therein without departing from the spirit and scope of the invention as defined by the following claims.

What is claimed is:

1. A device for extracting a mass from a patient's body, the device comprising:
   a coaxial tube assembly including an inner tube and an outer tube that are coaxially arranged and that define a proximal end and a distal end that is positionable within the body when the proximal end is positioned outside of the body, wherein the inner tube defines a lumen and the outer tube cooperates with the inner tube to define a coaxial annular space;
   a bag that receives therein the mass to be extracted;
   a bag-translating assembly including a coupling and a lead-screw mechanism, wherein the coupling couples to the bag and translates within the annular space of the coaxial tube assembly to move the bag from a deployed position within the body, through a retracting motion, and to a retracted position within the annular space, wherein as the bag is moved through the retracting motion the mass in the bag is pulled at least partially into the lumen at the distal end of the coaxial tube assembly, and wherein the lead-screw mechanism includes mating screw threads on an inner surface of the coupling and on an outer surface of the inner tube and includes conforming non-circular profiles defined by an outer surface of the coupling and an inner surface of the outer tube so that, upon application of a rotary force to the inner tube, the coupling is constrained by the conforming non-circular profiles from rotational movement relative to the outer tube and the rotationally constrained coupling translates along the inner tube impelled by the relative rotation of the mating screw threads; and
   a drive assembly including at least one actuator that is adapted to activate the bag-translating assembly to move the bag from the deployed position to the retracted position.

2. The device of claim 1, wherein the bag is received in the coaxial tube assembly only in the annular space, and further comprising a de-bulking tool that is received in the coaxial tube assembly only in the lumen.

3. The device of claim 1, wherein the bag has a mounting opening that couples to the coupling and at least one mass opening that receives the mass therethrough.

4. The device of claim 3, wherein the bag has a proximal end and the at least one mass opening is positioned adjacent the proximal end of the bag.

5. The device of claim 3, wherein the bag further comprises at least one closure adapted to manually close the mass opening.

6. The device of claim 1, wherein the bag has a single combination mounting/mass opening that couples to the coupling and that receives the mass therethrough.

7. The device of claim 1, wherein the bag couples to the coupling of the bag-translating assembly to enclose the distal end of the lumen of the coaxial tube assembly.

8. The device of claim 1, wherein the at least one actuator is operably coupled to the inner tube and is operable to impart the rotary force to the inner tube.

9. The device of claim 1, further comprising a de-bulking tool that is received in the lumen of the coaxial tube assembly, wherein as the bag is moved through the retracting motion the mass in the bag is pulled into engagement with the de-bulking tool to morcellate the mass into bits.

10. The device of claim 9, wherein the de-bulking tool has a sharp cutting head that morcellates the mass into the bits.

11. The device of claim 9, wherein the de-bulking tool has a helical ridge extending along it the length of the inner tube that, when the de-bulking tool is rotated, conveys the mass bits through the lumen from the distal end of the coaxial tube assembly, to outside of the body, and out of the proximal end of the coaxial tube assembly.

12. The device of claim 9, wherein the drive assembly is operably coupled to and drives the de-bulking tool and includes a linkage mechanism that is adapted so that the drive assembly drives the de-bulking tool and the bag-translating assembly contemporaneously.

13. The device of claim 9, further comprising a waste receptacle that is coupled to the coaxial tube assembly and that receives the morcellated mass bits.

14. The device of claim 1, wherein the bag is movable to the deployed position from a ready position in which the bag is coupled to the bag-translating coupling and positioned within the annular space of the coaxial tube assembly.

15. A device for extracting a mass from a patient's body, the device comprising:
  a coaxial tube assembly including an inner tube and an outer tube that are coaxially arranged and define a proximal end and a distal end that is positionable within the body when the proximal end is positioned outside of the body, wherein the inner tube defines a lumen and the outer tube cooperates with the inner tube to define an annular space;
  a de-bulking tool that is received in the lumen of the coaxial tube assembly, wherein the de-bulking tool has a cutting head with a fixed axial position relative to the distal end of the inner tube;
  a bag that receives therein the mass to be extracted;
  a bag-translating assembly including a coupling that the bag is mounted to so that the distal end of the lumen is enclosed and that translates within the annular space of the coaxial tube assembly to move the bag from a ready position within the annular space, to a deployed position within the body, through a retracting motion, and to a retracted position within the annular space, wherein as the bag is moved through the retracting motion the mass in the bag is pulled at least partially into the lumen at the distal end of the coaxial tube assembly and into engagement with the cutting head of the de-bulking tool to morcellate the mass into bits;
  a waste receptacle that is coupled to the proximal end of the coaxial tube assembly and that receives the morcellated mass bits; and
  a drive assembly including at least one actuator and a linkage mechanism, wherein the drive assembly drives the de-bulking tool and the bag-translating assembly contemporaneously.

16. The device of claim 15, wherein the bag has a mounting opening that couples to the bag-translating assembly and at least one mass opening that receives the mass therethrough.

17. The device of claim 15, wherein the bag-translating assembly includes a lead-screw mechanism that includes mating screw threads on an inner surface of the coupling and on an outer surface of the inner tube and includes conforming non-circular profiles defined by an outer surface of the coupling and an inner surface of the outer tube so that, upon application of a rotary force to the inner tube, the coupling is constrained by the conforming non-circular profiles from rotational movement relative to the outer tube and the rotationally constrained coupling translates along the inner tube impelled by the relative rotation of the mating screw threads.

18. The device of claim 15, wherein the de-bulking tool has a helical ridge extending along it the length of the inner tube that, when the de-bulking tool is rotated, conveys the mass bits through the lumen from the distal end of the coaxial tube assembly, to outside of the body, and out of the proximal end of the coaxial tube assembly.

19. A device for extracting a mass from a patient's body, the device comprising:
  a coaxial tube assembly including an inner tube and an outer tube that are coaxially arranged and that define a proximal end and a distal end that is positionable within the body when the proximal end is positioned outside of the body, wherein the inner tube defines a lumen and the outer tube cooperates with the inner tube to define a coaxial annular space;
  a de-bulking tool that is received in the lumen of the coaxial tube assembly, wherein the de-bulking tool has a cutting head with a fixed axial position relative to the distal end of the inner tube;
  a bag that receives therein the mass to be extracted and is received in the coaxial tube assembly in the annular space;
  a bag-translating assembly including a coupling that the bag is mounted to with the distal end of the lumen of the coaxial tube assembly enclosed within the bag and that translates within the annular space of the coaxial tube assembly to move the bag from a deployed position within the body, through a retracting motion, and to a retracted position within the annular space, wherein as the bag is moved through the retracting motion the mass in the bag is pulled at least partially into the lumen at the distal end of the coaxial tube assembly and into engagement with the cutting head of the de-bulking tool to morcellate the mass into bits; and
  a drive assembly including at least one actuator that is adapted to activate the bag-translating assembly to move the bag from the deployed position to the retracted position.

20. The device of claim 19, wherein the bag-translating assembly includes a lead-screw mechanism including mating screw threads on an inner surface of the coupling and on an outer surface the inner tube and includes conforming non-circular profiles defined by an outer surface of the coupling and an inner surface of the outer tube so that, upon application of a rotary force to the inner tube, the coupling is constrained by the conforming non-circular profiles from rotational movement relative to the outer tube and the rotationally constrained coupling translates along the inner tube impelled by the relative rotation of the mating screw threads.

21. The device of claim 19, wherein the at least one actuator is operably coupled to the inner tube and is operable to impart the rotary force to the inner tube.

22. The device of claim 19, wherein the de-bulking tool has a helical ridge extending along it the length of the inner tube that, when the de-bulking tool is rotated, conveys the mass bits through the lumen from the distal end of the coaxial tube assembly, to outside of the body, and out of the proximal end of the coaxial tube assembly.

23. The device of claim 22, further comprising a waste receptacle that is coupled to the proximal end of the coaxial tube assembly and that receives the morcellated mass bits.

24. The device of claim 19, wherein the bag is received in the coaxial tube assembly in the annular space and the de-bulking tool is received in the coaxial tube assembly only in the lumen.

25. The device of claim 19, wherein the drive assembly is operably coupled to and drives the de-bulking tool and includes a linkage mechanism that is adapted so that the drive assembly drives the de-bulking tool and the bag-translating assembly contemporaneously.

26. The device of claim 19, wherein the bag is movable to the deployed position from a ready position in which the bag is coupled to the bag-translating coupling and positioned within the annular space of the coaxial tube assembly.

27. The device of claim 19, wherein a proximal end of the bag is received in the coaxial tube assembly only in the annular space and the de-bulking tool is received in the coaxial tube assembly only in the lumen.

* * * * *